US007022696B2

(12) United States Patent
Grundler et al.

(10) Patent No.: US 7,022,696 B2
(45) Date of Patent: Apr. 4, 2006

(54) PIPERAZINO-DERIVATIVES AND THEIR USE AS PDE4 INHIBITOR

(75) Inventors: Gerhard Grundler, Constance (DE); Beate Schmidt, Allensbach (DE); Geert Jan Sterk, Utecht (NL)

(73) Assignee: Altana Pharma AG, Constance (DE)

(*) Notice: Subject to any disclaimer, the term of this patent is extended or adjusted under 35 U.S.C. 154(b) by 165 days.

(21) Appl. No.: 10/475,656

(22) PCT Filed: Apr. 24, 2002

(86) PCT No.: PCT/EP02/04494

§ 371 (c)(1),
(2), (4) Date: Oct. 23, 2003

(87) PCT Pub. No.: WO02/085885

PCT Pub. Date: Oct. 31, 2002

(65) Prior Publication Data

US 2004/0132721 A1    Jul. 8, 2004

(30) Foreign Application Priority Data

Apr. 25, 2001 (EP) .................. 01110227

(51) Int. Cl.
A61K 31/551 (2006.01)
A61K 31/496 (2006.01)
C07D 403/10 (2006.01)
(52) U.S. Cl. ............... 514/218; 514/237; 540/575; 544/237
(58) Field of Classification Search ............. 544/237; 540/575; 514/218, 248
See application file for complete search history.

(56) References Cited

U.S. PATENT DOCUMENTS

| 5,716,954 | A | 2/1998 | Wilhelm et al. |
| 5,859,008 | A | 1/1999 | Jonas et al. |
| 6,103,718 | A | 8/2000 | Sterk |
| 6,255,303 | B1 | 7/2001 | Sterk |
| 6,380,196 | B1 | 4/2002 | Ulrich et al. |
| 6,544,993 | B1 | 4/2003 | Sterk |
| 2004/0127707 | A1* | 7/2004 | Sterk .................. 544/116 |

FOREIGN PATENT DOCUMENTS

| EP | 0763534 | 9/1996 |
| EP | 0934933 | 8/1999 |
| WO | WO 93/07146 | 4/1993 |
| WO | WO 94/12461 | 6/1994 |
| WO | WO 98/31674 | 7/1998 |
| WO | WO 99/31071 | 6/1999 |
| WO | WO 99/31090 | 6/1999 |
| WO | WO99/47505 | 9/1999 |
| WO | WO 01/19818 | 3/2001 |
| WO | WO 01/30766 | 5/2001 |
| WO | WO 01/30777 | 5/2001 |
| WO | WO 01/94319 | 12/2001 |

OTHER PUBLICATIONS

Dyke et al. Expert Opin. Investig.Drugs, vol. 11(1), p. 1-13 (2002).*
U.S. Appl. No. 10/467,832, filed Aug. 13, 2003, Grundler et al.
U.S. Appl. No. 10/475,657, filed Oct. 23, 2003, Sterk.
Van der Mey, et al., "Novel Selective PDE4 Inhibitors. 1. Synthesis, Structure—Activity Relationships, and Molecular Modeling of 4-(3,4-dimethoxyphenyl)-2H phthalazin-1-ones and Analogues", J. Med. Chem., 44, p. 2511-2522 (2001).
Van der Mey, et al., "Novel Selective PDE4 Inhibitors. 2. Synthesis and Structure—Activity Relationships of 4-Aryl-Substituted cis-tetra and cis-Hexahydrophthalazinones", J. Med. Chem., 44, p. 2523-2535 (2001).
Van der Mey, et al., "Novel Selective PDE4 Inhibitors. 3. In vivo Antiinflammatory Activity of a New Series of N-Substituted cis-Tetra and cis-Hexahydrophthalazinones", J. Med. Chem., 45, p. 2520-2525 (2002).
Van der Mey, et al., "Novel Selective Phosphodiesterase (PDE4) Inhibitors. 4. Resolution, Absolute Configuration and PDE4 Inhibitory Activity of cis-Tetra and cis-Hexahydrophthalazinones", J. Med. Chem., 45, p. 2526-2533 (2002).
Patent Abstracts of Japan, JP01019077A, Jan. 23, 1989.
Montana, et al. "Phosphodiesterase 4 Inhibitors" *Cardiovascular and Pulmonary Diseases*, Chapter 5, pp. 41-56 (2001).
Souness, et al. "Immunosuppresive and anti-inflammatory effects of cyclic AMP phosphodiesterase (PDE) type 4 inhibitors", *Immunopharmacology* 47 (2000) pp. 127-162.

* cited by examiner

*Primary Examiner*—Emily Bernhardt
(74) *Attorney, Agent, or Firm*—Nath & Associates; Joshua B. Goldberg; Sheldon M. McGee

(57) ABSTRACT

The compounds of formula I

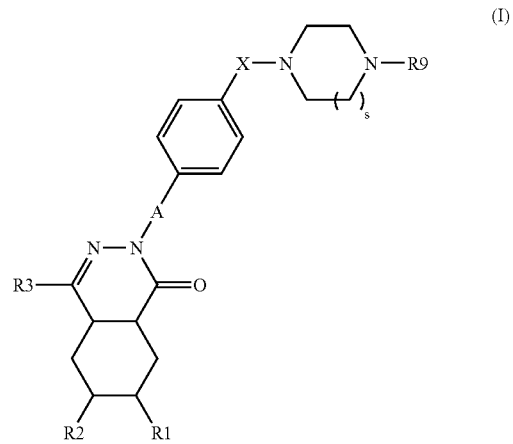

in which R1, R2, R3, A, X, s and R9 have the meanings as given in the description are novel effective PDE4 inhibitors.

14 Claims, No Drawings

PIPERAZINO-DERIVATIVES AND THEIR USE AS PDE4 INHIBITOR

FIELD OF APPLICATION OF THE INVENTION

The invention relates to novel piperazino-derivatives, which are used in the pharmaceutical industry for the production of medicaments.

KNOWN TECHNICAL BACKGROUND

International Patent Applications WO98/31674, WO99/31071, WO99/31090 and WO99/47505 disclose phthalazinone derivatives having selective PDE4 inhibitory properties. In the International patent application WO01/19818 phthalazinone derivatives with PDE3/4 inhibitory properties are disclosed. In the International Patent Application WO94/12461 and in the European Patent Application EP 0 763 534 3-aryl-pyridazin-6-one and arylalkyl-diazinone derivatives are described as selective PDE4 inhibitors.

DESCRIPTION OF THE INVENTION

It has now been found that the piperazino-derivatives, which are described in greater details below, have surprising and particularly advantageous properties.

The invention thus relates to compounds of formula I

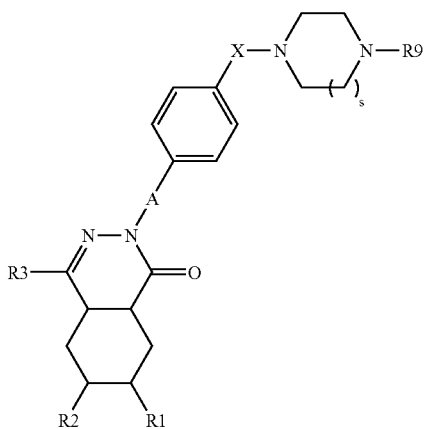

(I)

in which

R1 and R2 are both hydrogen or together form an additional bond,

R3 represents a benzene derivative of formula (a) or (b)

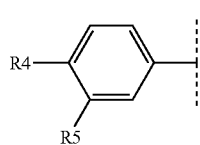

(a)

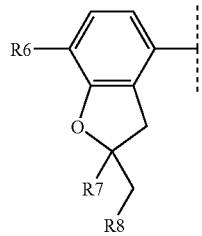

(b)

wherein

R4 is 1–4C-alkoxy or 1–4C-alkoxy which is completely or predominantly substituted by fluorine, R5 is 1–8C-alkoxy, 3–7C-cycloalkoxy, 3–7C-cycloalkylmethoxy, or 1–4C-alkoxy which is completely or predominantly substituted by fluorine, R6 is 1–4C-alkoxy, 3–5C-cycloalkoxy, 3–5C-cycloalkylmethoxy, or 1–4C-alkoxy which is completely or predominantly substituted by fluorine, R7 is 1–4C-alkyl and R8 is hydrogen or 1–4C-alkyl, or wherein R7 and R8 together and with inclusion of the two carbon atoms, to which they are bonded, form a spiro-linked 5-, 6- or 7-membered hydrocarbon ring, optionally interrupted by an oxygen or sulphur atom, A is a bond or methylene (—CH$_2$—), R9 is —C(O)R10, —(CH$_2$)$_m$—C(O)R11, —(CH$_2$)$_n$R12, Aryl, Hetaryl, phenylprop-1-en-3-yl or 1-methylpiperidin-4-yl, R10 hydrogen, 1–4C-alkyl, —OR13, furanyl, indolyl, phenyl, pyridyl, phenyl substituted by R16 and/or R17 or pyridyl substituted by R18 and/or R19, R11 is —N(R14)R15, R12 is —N(R14)R15, tetrahydrofuranyl or pyridinyl, R13 is 1–4C-alkyl, R14 is hydrogen, 1–4C-alkyl, 3–7C-cycloalkyl or 3–7C-cycloalkylmethyl, R15 is hydrogen, 1–4C-alkyl, 3–7C-cycloalkyl or 3–7C-cycloalkylmethyl, or R14 and R15 together and with inclusion of the nitrogen atom to which they are bonded, form a 4-morpholinyl-, 1-pyrrolidinyl-, 1-piperidinyl- or 1-hexahydroazepinyl-ring, Aryl is phenyl, pyridyl, pyrimidinyl, phenyl substituted by R16 and/or R17, pyridyl substituted by R18 and/or R19, R16 is halogen, nitro, 1–4C-alkyl, trifluoromethyl or 1–4C-alkoxy, R17 is halogen or 1–4C-alkyl, R18 is halogen, nitro, 1–4C-alkyl, trifluoromethyl or 1–4C-alkoxy, R19 is halogen or 1–4C-alkyl, Hetaryl is indol-4-yl, 2-methyl-quinolin-4-yl, 5-chloro-6-oxo-1-phenyl-1,6-dihydro-pyridazin-4-yl, 3-phenyl-1,2,4-thiadiazol-5-yl or 3-o-tolyl-1,2,4-thiadiazol-5-yl, n is an integer from 1 to 4, m is an integer from 1 to 4, s is an integer from 1 to 2, X is —C(O)— or —S(O)$_2$—, and the salts of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, ethoxy and methoxy radicals.

1–8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

Halogen within the meaning of the present invention is bromine, chlorine or fluorine.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

3–5C-Cycloalkoxy stands for cyclopropyloxy, cyclobutyloxy and cyclopentyloxy.

3–5C-Cycloalkylmethoxy stands for cyclopropylmethoxy, cyclobutylmethoxy and cyclopentylmethoxy.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

If R1 and R2 together form an additional bond, then the carbon atoms to which R1 and R2 are attached are linked to one another via a double bond.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compound of formula I to be emphasized are those in which

R1 and R2 are both hydrogen or together form an additional bond,

R3 represents a benzene derivative of formula (a) or (b)

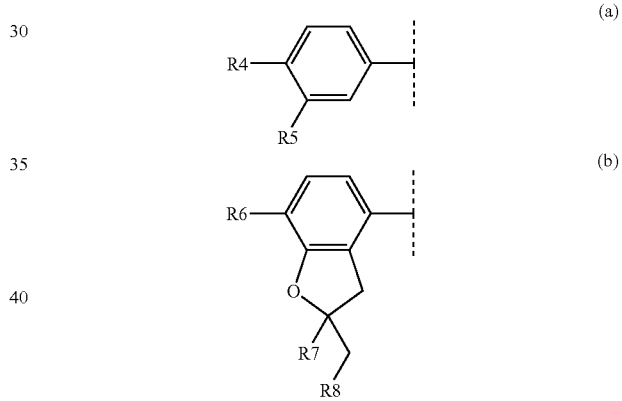

wherein
R4 is 1–2C-alkoxy or 1–2C-alkoxy which is completely or predominantly substituted by fluorine,
R5 is 1–4C-alkoxy,
R6 is 1–2C-alkoxy or 1–2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofurane or tetrahydropyran ring,
A is a bond or methylene (—CH$_2$—),
R9 is —C(O)R10, —(CH$_2$)$_m$—C(O)R11, —(CH$_2$)$_n$R12, Aryl, Hetaryl, phenylprop-1-en-3-yl or 1-methylpiperidin-4-yl,
R10 hydrogen, 1–4C-alkyl, —OR13, furanyl, indolyl, pyridyl or pyridyl substituted by R18 and/or R19,
R11 is —N(R14)R15,
R12 is —N(R14)R15, tetrahydrofuranyl or pyridinyl, R13 is 1–4C-alkyl,
R14 is hydrogen, 1–4C-alkyl, 3–7C-cycloalkyl or 3–7C-cycloalkylmethyl,
R15 is hydrogen, 1–4C-alkyl, 3–7C-cycloalkyl or 3–7C-cycloalkylmethyl,
or R14 and R15 together and with inclusion of the nitrogen atom to which they are bonded, form a 4-morpholinyl-, 1-pyrrolidinyl-, 1-piperidinyl- or 1-hexahydroazepinyl-ring,
Aryl is phenyl, pyridyl, pyrimidinyl, phenyl substituted by R16 and/or R17, pyridyl substituted by R18 and/or R19,
R16 is halogen, nitro, 1–4C-alkyl, trifluoromethyl or 1–4C-alkoxy,
R17 is halogen or 1–4C-alkyl,
R18 is halogen, nitro, 1–4C-alkyl, trifluoromethyl or 1–4C-alkoxy,
R19 is halogen or 1–4C-alkyl,
Hetaryl is indol-4-yl, 2-methyl-quinolin-4-yl, 5-chloro-6-oxo-1-phenyl-1,6-dihydro-pyridazin-4-yl, 3-phenyl-1,2,4-thiadiazol-5-yl or 3-o-tolyl-1,2,4-thiadiazol-5-yl,
n is an integer from 1 to 4,
m is an integer from 1 to 4,
s is 1,
X is —C(O)— or —S(O)$_2$—,
and the salts of these compounds.

Preferred compounds of formula I are those in which
R1 and R2 together form an additional bond,
R3 represents a benzene derivative of formula (a) or (b)

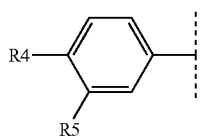

(a)

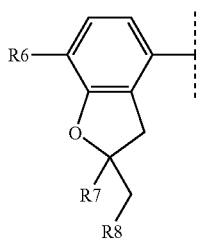

(b)

wherein
R4 is methoxy or ethoxy,
R5 is methoxy or ethoxy,
R6 is methoxy,
R7 is methyl and
R8 is hydrogen,
or wherein
R7 and R8 together and with inclusion of the two carbon atoms, to which they are bonded, form a cyclopentane or cyclohexane ring,
A is a bond or methylene (—CH$_2$—),
R9 is phenyl, pyrid-2-yl, pyrid-4-yl, pyrimidin-2-yl, 3-dimethylaminopropyl, 2-dimethylaminoethyl, dimethylaminocarbonylmethyl, furan-2-yl-methanoyl, formyl, ethoxycarbonyl, 5-nitropyridin-2-yl, 3,5-dichloropyridin-4-yl, 2-(morpholin-4-yl)ethyl, 3-(morpholin-4-yl)propyl, 2-morpholin-4-yl-2-oxo-ethyl, 2-oxo-2-pyrrolidin-1-yl-ethyl, 1H-indol-4-yl, tetrahydrofuran-2-ylmethyl, 2-(pyrrolidin-1-yl)ethyl, pyridin-4-ylmethyl, 2-methyl-quinolin-4-yl, 1-methyl-piperidin-4-yl, 5-trifluoromethyl-pyridin-2-yl, 5-chloro-6-oxo-1-phenyl-1,6-dihydro-pyridazin-4-yl, 3-phenyl-1,2,4-thiadiazol-5-yl, 3-o-tolyl-1,2,4-thiadiazol-5-yl or (E)-3-phenylallyl,
s is 1,
X is —C(O)— or —S(O)$_2$—,
and the salts of these compounds.

Particularly preferred compounds of formula I are those in which
R1 and R2 together form an additional bond,
R3 represents a benzene derivative of formula (a) or (b)

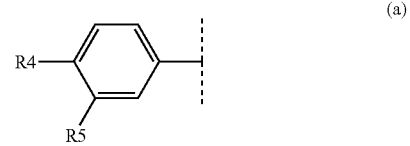

(a)

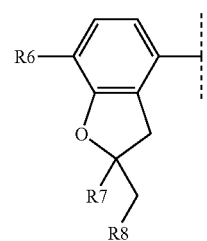

(b)

wherein
R4 is methoxy or ethoxy,
R5 is methoxy or ethoxy,
R6 is methoxy,
R7 is methyl and
R8 is hydrogen,
A is a bond,
R9 is phenyl, pyrid-2-yl, pyrid-4-yl, 3-dimethylaminopropyl, 2-dimethylaminoethyl, dimethylaminocarbonylmethyl, furan-2-yl-methanoyl, formyl, ethoxycarbonyl, 5-nitropyridin-2-yl, 3,5-dichloropyridin-4-yl, 2-(morpholin-4-yl)ethyl, 3-(morpholin-4-yl)propyl, 2-morpholin-4-yl-2-oxo-ethyl, 2-oxo-2-pyrrolidin-1-yl-ethyl, 1H-indol-4-yl, tetrahydrofuran-2-ylmethyl, 2-(pyrrolidin-1-yl)ethyl, pyridin-4-yl-methyl, 2-methyl-quinolin-4-yl, 1-methyl-piperidin-4-yl, 5-trifluoromethyl-pyridin-2-yl, 5-chloro-6-oxo-1-phenyl-1,6-dihydro-pyridazin-4-yl, 3-phenyl-1,2,4-thiadiazol-5-yl, 3-o-tolyl-1,2,4-thiadiazol-5-yl or (E)-3-phenylallyl,
s is 1,
X is —C(O)—,
and the salts of these compounds.

Further particularly preferred compounds of formula I are those in which
R1 and R2 together form an additional bond,
R3 represents a benzene derivative of formula (b)

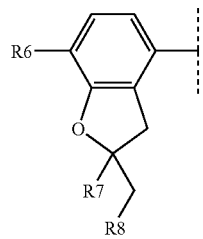

wherein
R6 is methoxy,
R7 is methyl and
R8 is hydrogen,
A is methylene (—CH$_2$—),
R9 is pyrimidin-2-yl, 3-dimethylaminopropyl or 2-(morpholin-4-yl)ethyl,
s is 1,
X is —C(O)—,
and the salts of these compounds.

A preferred embodiment of compounds of formula I are
(4aS,8aR)-4-(3,4-Diethoxyphenyl)-2-{4-[1-(4-phenyl-piperazin-1-yl)-methanoyl]-phenyl}-4a,5,8,8a-tetrahydro-2H-phthalazin-1-one,
(4aS,8aR)-4-(3,4-Diethoxyphenyl)-2-{4-[1-(4-pyridin-2-yl-piperazin-1-yl)-methanoyl]-phenyl}-4a,5,8,8a-tetrahydro-2H-phthalazin-1-one,
(4aS,8aR)-4-(3,4-Diethoxyphenyl)-2-(4-{1-[4-(3-dimethylamino-propyl)-piperazin-1-yl]-methanoyl}phenyl)-4a,5,8,8a-tetrahydro-2H-phthalazin-1-one,
(4aS,8aR)-4-(3,4-Diethoxyphenyl)-2-(4-{1-[4-(1-furan-2-yl-methanoyl)-piperazin-1-yl]-methanoyl}-phenyl)-4a,5,8,8a-tetrahydro-2H-phthalazin-1-one,
4-(1-{4-[(4aS,8aR)-4-(3,4-Diethoxyphenyl)-1-oxo-4a,5,8,8a-tetrahydro-1H-phthalazin-2-yl]-phenyl}-methanoyl)-piperazine-1-carbaldehyde,
(cis)-4-(3,4-Diethoxyphenyl)-2-[4-(4-pyridin-2-yl-piperazine-1-sulfonyl)-phenyl]-4a,5,8,8a-tetrahydro-2H-phthalazin-1-one,
4-(1-{4-[(4aS,8aR)-4-(3,4-Diethoxyphenyl)-1-oxo-4a,5,8,8a-tetrahydro-1H-phthalazin-2-yl]-phenyl}-methanoyl)-piperazine-1-carboxylic acid ethyl ester,
(4aS,8aR)-4-(7-methoxy-2,2-dimethyl-2,3-dihydro-benzofuran-4-yl)-2-(4-{1-[4-((E)-3-phenyl-allyl)-piperazin-1-yl]-methanoyl}-phenyl)-4a,5,8,8a-tetrahydro-2H-phthalazin-1-one,
(4aS,8aR)-2-(4-{1-[4-(1-furan-2-yl-methanoyl)-piperazin-1-yl]-methanoyl}-phenyl)-4-(7-methoxy-2,2-dimethyl-2,3-dihydro-benzofuran-4-yl)-4a,5,8,8a-tetrahydro-2H-phthalazin-1-one,
(4aS,8aR)-4-(7-Methoxy-2,2-dimethyl-2,3-dihydro-benzofuran-4-yl)-2-{4-[1-(4-phenyl-piperazin-1-yl)-methanoyl]-phenyl}-4a,5,8,8a-tetrahydro-2H-phthalazin-1-one,
(4aS,8aR)-2-(4-{1-[4-(3-Dimethylamino-propyl)-piperazin-1-yl]-methanoyl}-phenyl)-4-(7-methoxy-2,2-dimethyl-2,3-dihydro-benzofuran-4-yl)-4a,5,8,8a-tetrahydro-2H-phthalazin-1-one,
(4aS,8aR)-2-{4-[4-(5-Chloro-6-oxo-1-phenyl-1,6-dihydro-pyridazin-4-yl)-piperazine-1-carbonyl]-phenyl}-4-(3,4-diethoxy-phenyl)-4a,5,8,8a-tetrahydro-2H-phthalazin-1-one,
(4aS,8aR)-4-(3,4-Dimethoxyphenyl)-2-(4-{1-[4-(3-dimethylamino-propyl)-piperazin-1-yl]-methanoyl}-phenyl)-4a,5,8,8a-tetrahydro-2H-phthalazin-1-one,
(4aS,8aR)-2-{4-[4-(2-Dimethylamino-ethyl)-piperazine-1-carbonyl]-phenyl}-4-(7-methoxy-2,2-dimethyl-2,3-dihydro-benzofuran-4-yl)-4a,5,8,8a-tetrahydro-2H-phthalazin-1-one,
(4aS,8aR)-2-{4-[4-(3,5-Dichloropyridin-4-yl)-piperazin-1-yl]-methanoyl}-phenyl)-4-(3,4-dimethoxyphenyl)-4a,5,8,8a-tetrahydro-2H-phthalazin-1-one,
(4aS,8aR)-4-(3,4-Diethoxyphenyl)-2-(4-{1-[4-(2-morpholin-4-yl-ethyl)-piperazin-1-yl]-methanoyl}-phenyl)-4a,5,8,8a-tetrahydro-2H-phthalazin-1-one,
(4aS,8aR)-4-(3,4-Diethoxyphenyl)-2-(4-{1-[4-(3-phenyl-1,2,4-thiadiazol-5-yl)-piperazin-1-yl]-methanoyl}-phenyl)-4a,5,8,8a-tetrahydro-2H-phthalazin-1-one,
(4aS,8aR)-4-(3,4-Diethoxyphenyl)-2-(4-{1-[4-(5-nitro-pyridin-2-yl)-piperazin-1-yl]-methanoyl}-phenyl)-4a,5,8,8a-tetrahydro-2H-phthalazin-1-one,
(4aS,8aR)-4-(3,4-Dimethoxyphenyl)-2-(4-{1-[4-(3-o-tolyl-1,2,4-thiadiazol-5-yl)-piperazin-1-yl]-methanoyl}-phenyl)-4a,5,8,8a-tetrahydro-2H-phthalazin-1-one,
(4aS,8aR)-4-(7-Methoxy-2,2-dimethyl-2,3-dihydro-benzofuran-4-yl)-2-(4-{1-[4-(2-morpholin-4-yl-ethyl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-(4-{1-[4-(1H-indol-4-yl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-(4-{1-[4-(3-morpholin-4-yl-propyl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-(4-{1-[4-(tetrahydrofuran-2-ylmethyl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-(4-{1-[4-(2-pyrrolidin-1-yl-ethyl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-{4-[1-(4-pyridin-4-ylmethyl-piperazin-1-yl)-methanoyl]-phenyl}-4a,5,8,8a-tetrahydro-2H-phthalazin-1-one,
(4aS,8aR)-4-(3,4-Diethoxy-phenyl)-2-(4-{1-[4-(2-methylquinolin-4-yl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-{4-[1-(4-pyridin-4-yl-piperazin-1-yl)-methanoyl]-phenyl}-4a,5,8,8a-tetrahydro-2H-phthalazin-1-one,
(4aS,8aR)-4-(3,4-Diethoxy-phenyl)-2-(4-{1-[4-(1-methyl-piperidin-4-yl)-piperazin-1-yl]-methanoyl}-phenyl)-4a,5,8,8a-tetrahydro-2H-phthalazin-1-one,
(4aS,8aR)-4-(3,4-Diethoxy-phenyl)-2-(4-{1-[4-(5-trifluoromethyl-pyridin-2-yl)-piperazin-1-yl]-methanoyl}-phenyl)-4a,5,8,8a-tetrahydro-2H-phthalazin-1-one,
2-[4-(1-{4-[(4aS,8aR)-4-(3,4-Dimethoxy-phenyl)-1-oxo-4a,5,8,8a-tetrahydro-1H-phthalazin-2-yl]-phenyl}-methanoyl)-piperazin-1-yl]-N,N-dimethyl-acetamide,
(4aS,8aR)-4-(3,4-Dimethoxy-phenyl)-2-(4-{1-[4-(2-morpholin-4-yl-2-oxo-ethyl)-piperazin-1-yl]-methanoyl}-phenyl)-4a,5,8,8a-tetrahydro-2H-phthalazin-1-one,
(cis)-4-(7-Methoxy-2,2-dimethyl-2,3-dihydro-benzofuran-4-yl)-2-(4-{1-[4-(2-morpholin-4-yl-ethyl)-piperazin-1-yl]-methanoyl}-benzyl)-4a,5,8,8a-tetrahydro-2H-phthalazin-1-one,
(cis)-2-(4-{1-[4-(3-Dimethylamino-propyl)-piperazin-1-yl]-methanoyl}-benzyl)-4-(7-methoxy-2,2-dimethyl-2,3-dihydro-benzofuran-4-yl)-4a,5,8,8a-tetrahydro-2H-phthalazin-1-one,
(4aS,8aR)-4-(3,4-Dimethoxy-phenyl)-2-(4-{1-[4-(2-oxo-2-pyrrolidin-1-yl-ethyl)-piperazin-1-yl]-methanoyl}-phenyl)-4a,5,8,8a-tetrahydro-2H-phthalazin-1-one, (cis)-4-(7-Methoxy-2,2-dimethyl-2,3-dihydro-benzofuran-4-yl)-2-[4-(1-2,3,5,6-tetrahydro-[1,2']bipyrazinyl-4-yl-methanoyl)-benzyl]-4a,5,8,8a-tetrahydro-2H-phthalazin-1-one, and the salts of these compounds.

A special embodiment of the compounds of the present invention include those compounds of formula I in which R1 and R2 together form an additional bond, R4 and R5 are 1–2C-alkoxy, R6 is methoxy, R7 is methyl, R8 is hydrogen and s is 1.

Another special embodiment of the compounds of the present invention include those compounds of formula I in which R1 and R2 together form an additional bond, R3 represents a benzene derivative of formula (a), R4 and R5 are 1–2C-alkoxy and s is 1.

A further special embodiment of the compounds of the present invention include those compounds of formula I in which A is a bond and s is 1.

Still another special embodiment of the compounds of the present invention include those compounds of formula I in which R1 and R2 together form an additional bond, s is 1 and X is —C(O)—.

Another further special embodiment of the compounds of the present invention include those compounds of formula I in which R1 and R2 together form an additional bond, s is 1 and R3 represents a benzene derivative of formula (b), wherein R6 is methoxy.

Yet another special embodiment of the compounds of the present invention include those compounds of formula I in which R1 and R2 together form an additional bond, s is 1, X is —C(O)— and R3 represents a benzene derivative of formula (b), wherein R6 is methoxy, R7 is methyl and R8 is hydrogen.

The compounds of formula I are chiral compounds. Chiral centers exist in the compounds of formula I in the positions 4a and 8a. In case R3 represents a benzene derivative of formula (b) there is one further chiral center in the dihydrofuran-ring, if the substituents —R7 and —CH2R8 are not identical. However, preferred are in this connection those compounds, in which the substituents —R7 and —CH2R8 are identical or together and with inclusion of the two carbon atoms to which they are bonded form a spiro-connected 5-, 6- or 7-membered hydrocarbon ring.

Numbering:

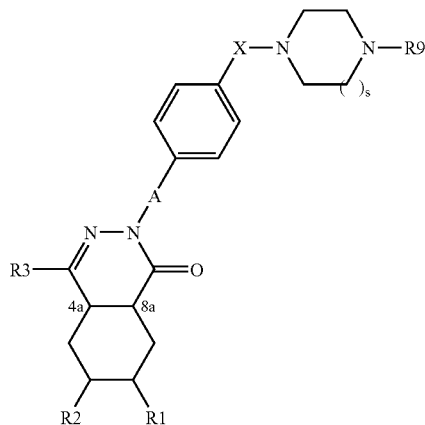

Therefore the invention includes all conceivable pure diastereomers and pure enantiomers of the compounds of formula I, as well as all mixtures thereof independent from the ratio, including the racemates. Preferred are those compounds of formula I, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a.

Racemates can be split up into the corresponding enantiomers by methods known by a person skilled in the art. Preferably the racemic mixtures are separated into two diastereomers during the preparation with the help of an optical active separation agent on the stage of the cyclohexanecarboxylic acids or the 1,2,3,6-tetrahydrobenzoic acids (for example, starting compounds A8, A9 and A10). As separation agents may be mentioned, for example, optical active amines such as the (+)- and (−)-forms of 1-phenylethylamine [(R)-(+)-1-phenylethylamine=D-α-methylbenzylamine or (S)-(−)-1-phenylethylamine=L-α-methylbenzylamine) and ephedrine, the optical active alkaloids quinine, cinchonine, cinchonidine and brucine.

The compounds according to the invention can be prepared, for example, as described in Reaction scheme 1.

Reaction scheme 1:

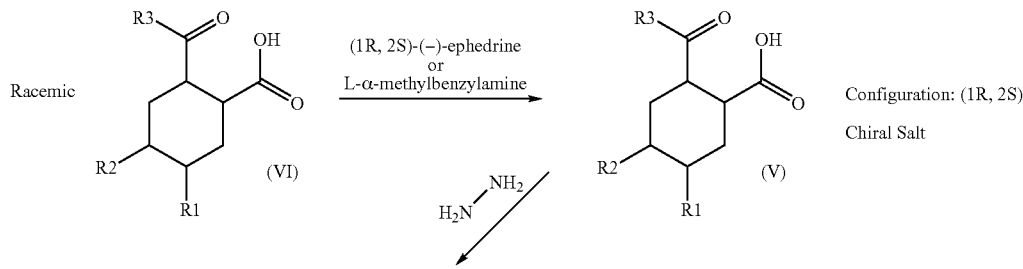

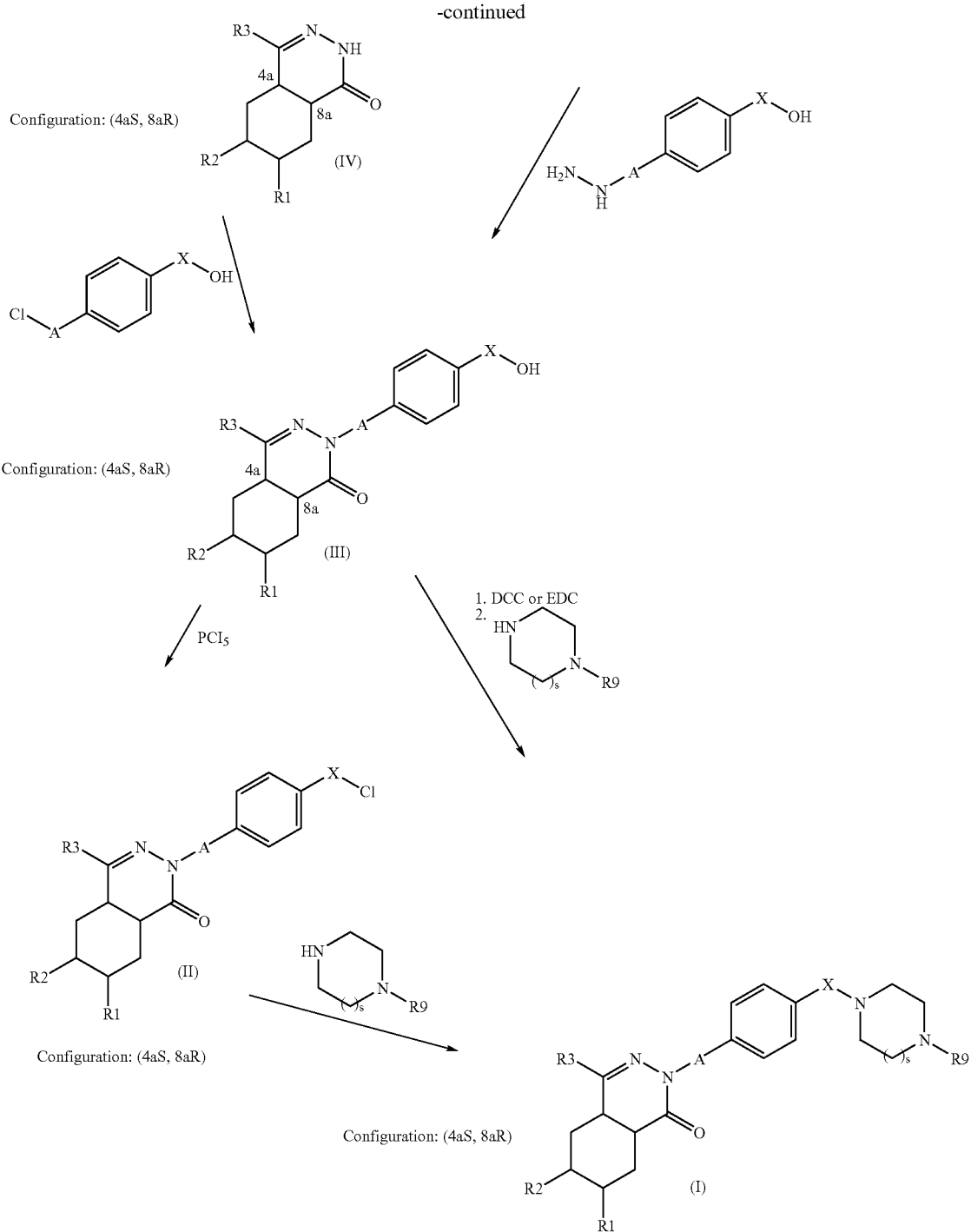

Reaction scheme 1 shows exemplarily the preparation of (4aS, 8aR)-configurated compounds of formula I. The (4aR, 8aS)-configurated compounds of formula I can be prepared analogously using in the first reaction step the antipodes of the optical amines shown in reaction scheme 1.

Starting from racemic (cis)-keto-1,2,3,4,5,6-hexahydrobenzoic- or racemic (cis)-keto-1,2,3,6-tetrahydrobenzoic acids of formula VI the two cis configurated enantiomeres are separated in form of their diastereomeric salts (compounds of formula V) with optical active amines such as the (+)- and (−)-forms of 1-phenylethylamine [(R)-(+)-1-phenylethylamine=D-α-methylbenzylamine or (S)-(−)-1-phenylethylamine=L-α-methylbenzylamine), ephedrine, the optical active alkaloids quinine, cinchonine, cinchonidine and brucine.

In a second reaction step the compounds of formula V are condensed with 4-hydrazinobenzoic acid or 4-hydrazino benzene sulfonic acid to give the compounds of formula III, in which A represents a bond. Alternatively, the compounds of formula V are first reacted with hydrazine to give the compounds of formula IV which then are reacted with 4-chloromethylbenzoic acid or 4-chloromethylbenzene sulfonic acid to give the compounds of formula III, in which A represents methylene (—CH$_2$—).

The compounds of formula III are activated by a chlorination agent like, for example, phosphorpentachloride (→compounds of formula II) or alternative by a suitable carbodiimide like, for example, DCC or EDC, and then are converted with a piperazine substituted by R9 (or a homopiperazine substituted by R9) to give the compounds of formula I.

Suitably, the conversions are carried out analogous to methods which are familiar per se to the person skilled in the art, for example, in the manner which is described in the following examples.

The substances according to the invention are isolated and purified in a manner known per se, e.g. by distilling off the solvent in vacuo and recrystallising the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final Products 1. (4aS,8aR)-4-(3,4-Diethoxyphenyl)-2-{4-[1-(4-phenyl-piperazin-1-yl)-methanoyl]-phenyl}-4a,5,8,8a-tetrahydro-2H-phthalazin-1-one hydrochloride A solution of 4 mmol of intermediate product A1 and 4 mmol of PCl$_5$ in 50 ml of dichloromethane is stirred for 30 min after which the solvent is evaporated. The residue is dissolved in 20 ml of tetrahydrofurane and added slowly to a solution of 3 mmol of 1-phenylpiperazine in 20 ml of pyridine. After stirring the resulting mixture for 30 min, the solvent is evaporated and the residue partitioned between aqueous sodium carbonate and ethyl acetate. The organic layer is dried over magnesium sulfate, after which a solution of hydrochloric acid in diethyl ether is added. The precipitate is filtered off and dried. M.p. 146–147° C.

2. (4aS,8aR)-4-(3,4-Diethoxyphenyl)-2-{4-[1-(4-pyridin-2-yl-piperazin-1-yl)-methanoyl]-phenyl}-4a,5,8,8a-tetrahydro-2H-phthalazin-1-one Prepared from intermediate product A1 and 1-(2-pyridyl) piperazine as described for compound 1. Cystallised from diethyl ether as the free base. M.p. 183–184° C.

3. (4aS,8aR)-4-(3,4-Diethoxyphenyl)-2-(4-{1-[4-(3-dimethylamino-propyl)-piperazin-1-yl]-methanoyl}-phenyl)-4a,5,8,8a-tetrahydro-2H-phthalazin-1-one dihydrochloride Prepared from intermediate product A1 and 1-(3-dimethylaminopropyl)piperazine as described for compound 1. Cystallised from diethyl ether as the free base. M.p. 248° C. (with decomposition).

4. (4aS,8aR)-4-(3,4-Diethoxyphenyl)-2-(4-{1-[4-(1-furan-2-yl-methanoyl)-piperazin-1-yl]-methanoyl}-phenyl)-4a,5,8,8a-tetrahydro-2H-phthalazin-1-one Prepared from intermediate product A1 and 1-(furan-2-yl-methanoyl)piperazine as described for compound 1. Cystallised from diethyl ether as the free base. M.p. 114–115° C.

5. 4-(1-{4-[(4aS,8aR)-4-(3,4-Diethoxyphenyl)-1-oxo-4a,5,8,8a-tetrahydro-1H-phthalazin-2-yl]-phenyl}-methanoyl)-piperazine-1-carbaldehyde Prepared from intermediate product A1 and piperazinylcarbaldehyde as described for compound 1. Cystallised from diethyl ether as the free base. M.p. 143–144° C.

6. (cis)-4-(3,4-Diethoxyphenyl)-2-[4-(4-pyridin-2-yl-piperazine-1-sulfonyl)-phenyl]-4a,5,8,8a-tetrahydro-2H-phthalazin-1-one Prepared from intermediate product A5 and 1-(2-pyridyl)-piperazine as described for compound 1. Cystallised from diethyl ether as the free base. M.p. 181–182° C.

7. 4-(1-{4-[(4aS,8aR)-4-(3,4-Diethoxyphenyl)-1-oxo-4a,5,8,8a-tetrahydro-1H-phthalazin-2-yl]-phenyl}-methanoyl)-piperazine-1-carboxylic acid ethyl ester Prepared from intermediate product A1 and 1-(ethoxycarbonyl)piperazine as described for compound 1. Cystallised from diethyl ether as the free base. M.p. 146–147° C.

8. (4aS,8aR)-4-(7-methoxy-2,2-dimethyl-2,3-dihydro-benzofuran-4-yl)-2-(4-{1-[4-((E)-3-phenyl-allyl)-piperazin-1-yl]-methanoyl}-phenyl)-4a,5,8,8a-tetrahydro-2H-phthalazin-1-one hydrochloride A mixture of 2 mmol of intermediate product A2, 2 mmol of 1-{(E)-3-phenyl-allyl}-piperazine and 3 mmol of 1-(3-dimethylaminopropyl)-3-ethylcarbodiimide hydrochloride in 30 ml of dimethylformamide is stirred for 18 h, after which the mixure is poored into aqueous sodium carbonate. This mixture is extracted with diethyl ether and the extract is dried over magnesium sulfate. Addition of a solution of hydrochloric acid in ether causes precipitation of the title compound. M.p. 230–231° C.

9. (4aS,8aR)-2-(4-{1-[4-(1-furan-2-yl-methanoyl)-piperazin-1-yl]-methanoyl}-phenyl)-4-(7-methoxy-2,2-dimethyl-2,3-dihydrobenzofuran-4-yl)-4a,5,8,8a-tetrahydro-2-phthalazin-1-one Prepared from intermediate product A2 and 1-(furan-2-yl-methanoyl)-piperazine as described for compound 8. Crystallised from diethyl ether as the free base. M.p. 138–140° C.

10. (4aS,8aR)-4-(7-Methoxy-2,2-dimethyl-2,3-dihydro-benzofuran-4-yl)-2-{4-[1-(4-phenyl-piperazin-1-yl)-methanoyl]-phenyl}-4a,5,8,8a-tetrahydro-2H-phthalazin-1-one Prepared from intermediate product A2 and 1-phenylpiperazine as described for compound 8. Crystallised from diethyl ether as the free base. M.p. 185–186° C.

11. (4aS,8aR)-2-(4-{1-[4-(3-Dimethylamino-propyl)-piperazin-1-yl]-methanoyl}-phenyl)-4-(7-methoxy-2,2-dimethyl-2,3-dihydro-benzofuran-4-yl)-4a,5,8,8a-tetrahydro-2H-phthalazin-1-one dihydrochloride Prepared from intermediate product A2 and 1-(3-dimethylaminopropyl)-piperazine as described for compound 8. M.p. 262° C. (with decomposition).

12. (4aS,8aR)-2-{4-[4-(5-Chloro-6-oxo-1-phenyl-1,6-dihydro-pyridazin-4-yl)-piperazine-1-carbonyl]-phenyl}-4-(3,4-diethoxy-phenyl)-4a,5,8,8a-tetrahydro-2H-phthalazin-1-one Prepared from intermediate product A1 and 1-(5-Chloro-6-oxo-1-phenyl-1,6-dihydro-pyridazin-4-yl)piperazine as described for compound 8. Crystallised from methanol. M.p. 148–151° C.

13. (4aS,8aR)-4-(3,4-Dimethoxyphenyl)-2-(4-{1-[4-(3-dimethylamino-propyl)-piperazin-1-yl]-methanoyl}-phenyl)-4a,5,8,8a-tetrahydro-2H-phthalazin-1-one dihydrochloride Prepared from intermediate product A6 and 1-(3-dimethylaminopropyl)piperazine as described for compound 8. M.p. 223–226° C.

14. (4aS,8aR)-2-{4-[4-(2-Dimethylamino-ethyl)-piperazine-1-carbonyl]-phenyl}-4-(7-methoxy-2,2-dimethy-2,3-dihydro-benzofuran-4-yl)-4a,5,8,8a-tetrahydro-2H-phthalazin-1-one dihydrochloride Prepared from intermediate product A2 and 1-(2-dimethylaminoethyl)-piperazine as described for compound 8. M.p. 245° C. (with decomposition).

15. (4aS,8aR)-2-(4-{1-[4-(3,5-Dichloropyridin-4-yl)-piperazin-1-yl]-methanoyl}-phenyl)-4-(3,4-dimethoxyphenyl)-4a,5,8,8a-tetrahydro-2H-phthalazin-1-one Prepared from intermediate product A6 and 1-(3,5-Dichloropyridin-4-yl)piperazine as described for compound 8. Crystallised as the free base from methanol. M.p. 137–139° C.

16. (4aS,8aR)-4-(3,4-Diethoxyphenyl)-2-(4-{1-[4-(2-morpholin-4-yl-ethyl)-piperazin-1-yl]-methanoyl}-phenyl)-4a,5,8,8a-tetrahydro-2H-phthalazin-1-one dihydrochloride Prepared from intermediate product A1 and 1-{2-(4-morpholino)ethyl}piperazine as described for compound 8. M.p. 255° C. (with decomposition).

17. (4aS,8aR)-4-(3,4-Diethoxyphenyl)-2-(4-{1-[4-(3-phenyl-1,2,4-thiadiazol-5-yl)-piperazin-1-yl]-methanoyl}-phenyl)-4a,5,8,8a-tetrahydro-2H-phthalazin-1-one Prepared from intermediate product A1 and 1-(3-phenyl-1,2,4-thiadiazol-5-yl)-piperazine as described for compound 8. Crystallised as the free base from diethyl ether. M.p. 168–169° C.

18. (4aS,8aR)-4-(3,4-Diethoxyohenyl)-2-(4-{1-[4-(5-nitro-pyridin-2-yl)-piperazin-1-yl]-methanoyl}-phenyl)-4a,5,8,8a-tetrahydro-2H-phthalazin-1-one hydrochloride Prepared from intermediate product A1 and 1-(5-nitropyridin-2-yl)-piperazine as described for compound 8. M.p. 117–118° C.

19. (4aS,8aR)-4-(3,4-Dimethoxyphenyl)-2-(4-{1-[4-(3-o-tolyl-1,2,4-thiadiazol-5-yl)-piperazin-1-yl]-methanoyl}-phenyl)-4a,5,8,8a-tetrahydro-2H-phthalazin-1-one hydrochloride Prepared from intermediate product A1 and 1-(3-o-tolyl-1,2,4-thiadiazol-5-yl)-piperazine as described for compound 8. M.p. 115–118° C.

20. (4aS,8aR)-4-(7-Methoxy-2,2-dimethyl-2,3-dihydro-benzofuran-4-yl)-2-(4-{1-[4-(2-morpholin-4-yl-ethyl)-piperazin-1-yl]-methanoyl}-phenyl)-4a,5,8,8a-tetrahydro-2H-phthalazin-1-one dihydrochloride Prepared from intermediate product A2 and 4-(2-piperazin-1-yl-ethyl)-morpholine as described for compound 8. M.p. 271° C. (decomposes).

21. (4aS,8aR)-4-(3,4-Diethoxy-phenyl)-2-(4-{1-[4-(1H-indol-4-yl)-piperazin-1-yl]-methanoyl}-phenyl)-4a,5,8,8a-tetrahydro-2H-phthalazin-1-one hydrochloride Prepared from intermediate product A1 and 4-piperazin-1-yl-1H-indole as described for compound 8. M.p. 142–145° C.

22. (4aS,8aR)-4-(3,4-Diethoxy-phenyl)-2-(4-{1-[4-(3-morpholin-4-yl-propyl)-piperazin-1-yl]-methanoyl}-phenyl)-4a,5,8,8a-tetrahydro-2H-phthalazin-1-one dihydrochloride Prepared from intermediate product A1 and 4-(3-piperazin-1-yl-propyl)-morpholine as described for compound 8. M.p. 170–171° C.

23. (4aS,8aR)-4-(3,4-Diethoxy-phenyl)-2-(4-{1-[4-(tetrahydro-furan-2-ylmethyl)-piperazin-1-yl]-methanoyl}-phenyl)-4a,5,8,8a-tetrahydro-2H-phthalazin-1-one hydrochloride Prepared from intermediate product A1 and 1-(tetrahydro-furan-2-ylmethyl)-piperazine as described for compound 8. M.p. 131–133° C.

24. (4aS,8aR)-4-(3,4-Diethoxy-phenyl)-2-(4-{1-[4-(2-pyrrolidin-1-yl-ethyl)-piperazin-1-yl]-methanoyl}-phenyl)-4a,5,8,8a-tetrahydro-2H-phthalazin-1-one dihydrochloride Prepared from intermediate product A1 and 1-(2-pyrrolidin-1-yl-ethyl)-piperazine as described for compound 8. M.p. 185–186° C.

25. (4aS,8aR)-4-(3,4-Diethoxy-phenyl)-2-{4-[1-(4-pyridin-4-ylmethyl-piperazin-1-yl)-methanoyl]-phenyl}-4a,5,8,8a-tetrahydro-2H-phthalazin-1-one dihydrochloride Prepared from intermediate product A1 and 1-pyridin-4-ylmethyl-piperazine as described for compound 8. M.p. 83–85° C.

26. (4aS,8aR)-4-(3,4-Diethoxy-phenyl)-2-(4-{1-[4-(2-methyl-quinolin-4-yl)-piperazin-1-yl]-methanoyl}-phenyl)-4a,5,8,8a-tetrahydro-2H-phthalazin-1-one hydrochloride Prepared from intermediate product A1 and 2-methyl-4-piperazin-1-yl-quinoline as described for compound 8. M.p. 203–206° C. (decomposes)

27. (4aS,8aR)-4-(3,4-Diethoxy-phenyl)-2-{4-[1-(4-pyridin-4-yl-piperazin-1-yl)-methanoyl]-phenyl}-4a,5,8,8a-tetrahydro-2H-phthalazin-1-one hydrochloride Prepared from intermediate product A1 and 1-pyridin-4-yl-piperazine as described for compound 8.
M.p. 164–167° C.

28. (4aS,8aR)-4-(3,4-Diethoxy-phenyl)-2-(4-{1-[4-(1-methyl-piperidin-4-yl)-piperazin-1-yl]-methanoyl}-phenyl)-4a,5,8,8a-tetrahydro-2H-phthalazin-1-one dihydrochloride Prepared from intermediate product A1 and 1-(1-methyl-piperidin-4-yl)-piperazine as described for compound 8. M.p. 275° C. (decomposes)

29. (4aS,8aR)-4-(3,4-Diethoxy-phenyl)-2-(4-{1-[4-(5-trifluoromethyl-pyridin-2-yl)-piperazin-1-yl]-methanoyl}-phenyl)-4a,5,8,8a-tetrahydro-2H-phthalazin-1-one Prepared from intermediate product A1 and 1-(5-trifluoromethyl-pyridin-2-yl)-piperazine as described for compound 8. M.p. 121–123° C.

30. 2-[4-(1-{4-[(4aS,8aR)-4-(3,4-Dimethoxy-phenyl)-1-oxo-4a,5,8,8a-tetrahydro-1H-phthalazin-2-yl]-phenyl}-methanoyl)-piperazin-1-yl]-N,N-dimethyl-acetamide hydrochloride Prepared from intermediate product A6 and N,N-dimethyl-2-piperazin-1-yl-acetamide as described for compound 8. M.p. 93–94° C.

31. (4aS,8aR)-4-(3,4-Dimethoxy-phenyl)-2-(4-{1-[4-(2-morpholin-4-yl-2-oxo-ethyl)-piperazin-1-yl]-methanoyl}-phenyl)-4a,5,8,8a-tetrahydro-2H-phthalazin-1-one hydrochloride Prepared from intermediate product A6 and 1-morpholin-4-yl-2-piperazin-1-yl-ethanone as described for compound 8. M.p. 168–169° C.

32. (cis)-4-(7-Methoxy-2,2-dimethyl-2,3-dihydro-benzofuran-4-yl)-2-(4-{1-[4-(2-morpholin-4-yl-ethyl)-piperazin-1-yl]-methanoyl}-benzyl)-4a,5,8,8a-tetrahydro-2H-phthalazin-1-one dihydrochloride Prepared from intermediate product A11 and 4-(2-piperazin-1-yl-ethyl)-morpholine as described for compound 8. M.p. 210–211° C.

33. (cis)-2-(4-{1-[4-(3-Dimethylamino-propyl)-piperazin-1-yl]-methanoyl}-benzyl)-4-(7-methoxy-2,2-dimethyl-2,3-dihydro-benzofuran-4-yl)-4a,5,8,8a-tetrahydro-2H-phthalazin-1-one dihydrochloride Prepared from intermediate product A11 and dimethyl-(3-piperazin-1-yl-propyl)-amine as described for compound 8. M.p. 247–249° C.

34. (4aS,8aR)-4-(3,4-Dimethoxy-phenyl)-2-(4-{1-[4-(2-oxo-2-pyrrolidin-1-yl-ethyl)-piperazin-1-yl]-methanoyl}-phenyl)-4a,5,8,8a-tetrahydro-2H-phthalazin-1-one hydrochloride Prepared from intermediate product A6 and 2-piperazin-1-yl-1-pyrrolidin-1-yl-ethanone as described for compound 8. M.p. 160–161° C.

35. (cis)-4-(7-Methoxy-2,2-dimethyl-2,3-dihydro-benzofuran-4-yl)-2-[4-(1-2,3,5,6-tetrahydro-[1,2']bipyrazinyl-4-yl-methanoyl)-benzyl]-4a,5,8,8a-tetrahydro-2H-phthalazin-1-one dihydrochloride Prepared from intermediate product A11 and 3,4,5,6-Tetrahydro-2H-[1,2']bipyrazinyl as described for compound 8. M.p. 124–126° C.

Starting Compounds and Intermediate Products

A1. (4aS,8aR)-4-(3,4-Diethoxyphenyl)-1-oxo-4a,5,8,8a-tetrahydro-1H-phthalazin-2-yl}benzoic acid A solution of 8 g of intermediate product A4 and 8 g of 4-hydrazinobenzoic acid in a mixture of 100 ml of 1-propanol and 5 ml of triethyl amine are refluxed for 18 h. After evaporating the solvent, the residue is partitioned between diluted hydrochloric acid and dichloromethane. The organic layer is dried over magnesium sulphate and evaporated. The residue is purified by chromatography (ethyl acetate). Crystallisation from diethyl ether. M.p. 204–207° C.

A2. 4-{(4aS,8aR)-4-(2,3-Dihydro-2,2-dimethyl-7-methoxybenzofuranyl)-1-oxo-4a,5,8,8a-tetrahydrophthalazin-2-yl}benzoic acid A solution of 10 g of intermediate product A3, 10 g of 4-hydrazinobenzoic acid and 3 g of pyridine hydrochloride in 50 ml of pyridine are refluxed for 18 h. After evaporating the solution, the residue is dissolved in ethyl acetate and washed 3 times with 1N hydrochloric acid. The solution is then dried over magnesium sulphate and evaporated. The title compound is crystallised from diethyl ether.
M.p. 212–214° C.

A3. (1R,2S)-2-(2,3-Dihydro-2,2-dimethyl-7-methoxybenzofuran-4-carbonyl)-1,2,3,6-tetrahydrobenzoic acid (1R,2S)-(−)-ephedrine salt A mixture of 10 mmol of starting compound A10 and 5 mmol of (1R,2S)-(−)-ephedrine in 150 ml of ethyl acetate is stirred for 18 h after which the precipitate is filtered off and dried.

A4. (1R,2S)-2-(3,4-Diethoxybenzoyl)-1,2,3,6-tetrahydrobenzoic acid (−)-α-methylbenzylamine salt A mixture of 10 mmol of starting compound A8 and 5 mmol of L-α-methylbenzylamine in 100 ml of ethyl acetate is stirred for 18 h after which the precipitate is filtered off and dried.

A5. (cis)-4-{4-(3,4-Diethoxyphenyl)-1-oxo-4a,5,8,8a-tetrahydro-1H-phthalazin-2-yl}benzenesulfonic acid A solution of 16 mmol of starting compound A8, 16 mmol of 4-hydrazino benzene sulfonic acid and 5 ml of triethyl amine in 100 ml of 1-propanol is refluxed for 6 h. After evaporating, the residue is dissolved in 100 ml of acetic acid and refluxed for 2 h. After evaporating, the residue is partitioned between 1 N hydrochloric acid and ethyl acetate. The organic layer is dried over magnesium sulfate and evaporated. The title compound is crystallised from diethyl ether. M.p. 65–69° C.

A6. (4aS,8aR)-4-(3,4-Dimethoxyphenyl)-1-oxo-4a,5,8,8a-tetrahydro-1H-phthalazin-2-yl}benzoic acid Prepared from intermediate product A7 as described for starting compound A1. Crystallised from diethyl ether. M.p. 185–186° C.

A7. (1R,2S)-2-(3,4-Dimethoxybenzoyl)-1,2,3,6-tetrahydrobenzoic acid (−)-α-methylbezylamine salt Prepared analogously as described for intermediate product A4 using starting compound A9 instead of A8.

A8. (cis)-2-(3,4-Diethoxybenzoyl)-1,2,3,6-tetrahydrobenzoic acid

Prepared as described in WO98/31674.

A9. (cis)-2-(3,4-Dimethoxybenzoyl)-1,2,3,6-tetrahydrobenzoic acid

Prepared as described in WO98/31674.

A10. (cis)-2-(2,3-Dihydro-2,2-dimethyl-7-methoxybenzofuran-4-carbonyl)-1,2,3,6-tetrahydrobenzoic acid Prepared as described in WO99/31090.

A11. (cis)-4-[4-(7-Methoxy-2,2-dimethyl-2,3-dihydro-benzofuran-4-yl)-1-oxo-4a,5,8,8a-tetrahydro-1H-phthalazin-2-ylmethyl]-benzoic acid To a solution of 0.05 mole of (cis)-4-(7-Methoxy-2,2-dimethyl-2,3-dihydro-benzofuran-4-yl)-4a,5,8,8a-tetrahydro-2H-phthalazin-1-one (starting compound A12) and 0.15 mole of sodium hydride in 100 ml of dimethylformamide is stirred at RT for 30 min, after which 0.05 mole of 4-chloromethylbenzoic acid is added. This mixture is left stirring for 18 h, after which it is poured into water. This solution is acidified with hydrochloric acid and subsequently extracted with dichloromethane. The organic solution is dried over magnesium sulfate and evaporated. The compound is crystallized from diethyl ether.
M.p. 219–220° C.

A12. (cis)-4-(7-Methoxy-2,2-dimethyl-2,3-dihydro-benzofuran-4-yl)-4a,5,8,8a-tetrahydro-2H-phthalazin-1-one Prepared as described in WO99/31090.

COMMERCIAL UTILITY

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by processes which are known per se and familiar to the person skilled in the art. As medicaments, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the medicaments according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg/kg per day.

BIOLOGICAL INVESTIGATIONS

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21–40, "The Handbook of Immunopharmacology", Academic Press, 1996), and its inhibition leads to an increase of the intracellular cAMP concentration and thus to the inhibition of cellular activation (J E Souness et al., Immunopharmacology 47: 127–162, 2000).

The antiinflammatory potential of PDE4 inhibitors in vivo in various animal models has been described (M M Teixeira, TiPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (D M Essayan, Biochem Pharmacol 57: 965–973, 1999). Substances which inhibit the secretion of the afore-mentioned proinflammatory mediators are those which inhibit PDE4. PDE4 inhibition by the compounds according to the invention is thus a central indicator for the suppression of inflammatory processes.

Method for Measuring Inhibition of PDE4 Activity

PDE4 activity was determined as described by Thompson et al. (Adv Cycl Nucl Res 10: 69–92, 1979) with some modifications (Bauer and Schwabe, Naunyn-Schmiedeberg's Arch Pharmacol 311: 193–198, 1980). At a final assay volume of 200 μl (96well microtiter plates) the assay mixture contained 20 mM Tris (pH 7.4), 5 mM $MgCl_2$, 0.5 μM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682–690, 1991); the PDE3-specific inhibitor Motapizone (1 μM) was included to suppress PDE3 activity originating from contaminating platelets. Serial dilutions of the compounds were prepared in DMSO and further diluted 1:100 (v/v) in the assays to obtain the desired final concentrations of the inhibitors at a DMSO concentration of 1% (v/v) which by itself only slightly affected PDE4 activity.

After preincubation for 5 min at 37° C., the reaction was started by the addition of substrate (cAMP) and the assays were incubated for further 15 min at 37° C. 50 μl of 0.2 N HCl was added to stop the reaction and the assays were left on ice for about 10 min. Following incubation with 25 μg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

For the following compounds inhibitory values [measured as $-\log IC_{50}$ (mol/l)] higher than 9 were determined. The numbers of the compounds correspond to the numbers of the examples.

Compounds 8–15 and 18–29.

What is claimed is:
1. A compound of formula I

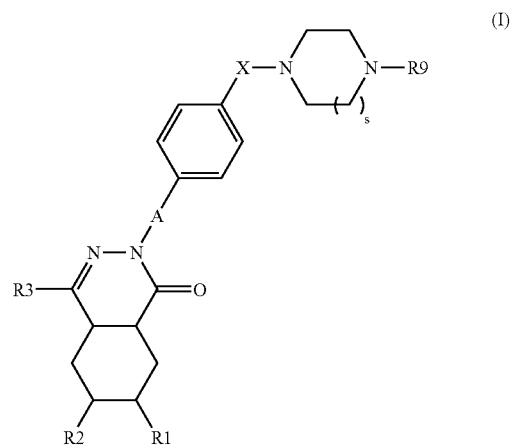

in which
R1 and R2 are both hydrogen or together form an additional bond,
R3 represents a benzene derivative of formula (a) or (b)

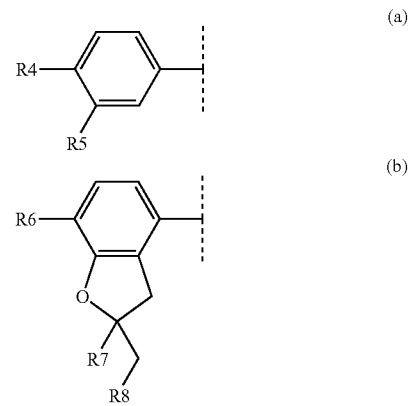

wherein
R4 is 1–4C-alkoxy or 1–4C-alkoxy which is completely or predominantly substituted by fluorine,
R5 is 1–8C-alkoxy, 3–7C-cycloalkoxy, 3–7C-cycloalkylmethoxy, or 1–4C-alkoxy which is completely or predominantly substituted by fluorine, R6 is 1–4C-alkoxy, 3–5C-cycloalkoxy, 3–5C-cycloalkylmethoxy, or 1–4C-alkoxy which is completely or predominantly substituted by fluorine, R7 is 1–4C-alkyl and R8 is hydrogen or 1–4C-alkyl, or wherein R7 and R8 together and with inclusion of the two carbon atoms, to which they are bonded, form a spiro-linked 5-, 6- or 7-membered hydrocarbon ring, optionally interrupted by an oxygen or sulphur atom, A is a bond or methylene (—CH$_2$—), R9 is —C(O)R10, —(CH$_2$)$_m$—C(O)R11, —(CH$_2$)$_n$R12, Aryl, Hetaryl, phenylprop-1-en-3-yl or 1-methyl-piperidin-4-yl, R10 hydrogen, 1–4C-alkyl, —OR13, furanyl, indolyl, phenyl, pyridyl, phenyl substituted by R16 and/or R17 or pyridyl substituted by R18 and/or R19, R11 is —N(R14)R15, R12 is —N(R14)R15, tetrahydrofuranyl or pyridinyl, R13 is 1–4C-alkyl, R14 is hydrogen, 1–4C-alkyl, 3–7C-cycloalkyl or 3–7C-cycloalkylmethyl, R15 is hydrogen, 1–4C-alkyl, 3–7C-cycloalkyl or 3–7C-cycloalkylmethyl, or R14 and R15 together and with inclusion of the nitrogen atom to which they are bonded, form a 4-morpholinyl-, 1-pyrrolidinyl-, 1-piperidinyl- or 1-hexahydroazepinyl-ring, Aryl is phenyl, pyridyl, pyrimidinyl, phenyl substituted by R16 and/or R17, pyridyl substituted by R18 and/or R19, R16 is halogen, nitro, 1–4C-alkyl, trifluoromethyl or 1–4C-alkoxy, R17 is halogen or 1–4C-alkyl, R18 is halogen, nitro, 1–4C-alkyl, trifluoromethyl or 1–4C-alkoxy, R19 is halogen or 1–4C-alkyl, Hetaryl is indol-4-yl, 2-methyl-quinolin-4-yl, 5-chloro-6-oxo-1-phenyl-1,6-dihydro-pyridazin-4-yl, 3-phenyl-1,2,4-thiadiazol-5-yl or 3-o-tolyl-1,2,4-thiadiazol-5-yl, n is an integer from 1 to 4, m is an integer from 1 to 4, s is an integer from 1 to 2, X is —C(O)— or —S(O)$_2$—, or a hydrate, salt, or hydrate of a salt thereof.

2. A compound of formula I according to claim 1 in which

R1 and R2 are both hydrogen or together form an additional bond,

R3 represents a benzene derivative of formula (a) or (b)

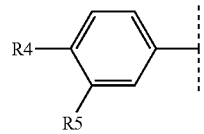
(a)

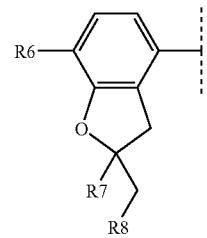
(b)

wherein

R4 is 1–2C-alkoxy or 1–2C-alkoxy which is completely or predominantly substituted by fluorine, R5 is 1–4C-alkoxy, R6 is 1–2C-alkoxy or 1–2C-alkoxy which is completely or predominantly substituted by fluorine, R7 is methyl and R8 is hydrogen, or wherein R7 and R8 together and with inclusion of the two carbon atoms, to which they are bonded, form a spiro-linked cyclopentane, cyclohexane, tetrahydrofurane or tetrahydropyran ring, A is a bond or methylene (—CH$_2$—), R9 is —C(O)R10, —(CH$_2$)$_m$—C(O)R11, —(CH$_2$)$_n$R12, Aryl, Hetaryl, phenylprop-1-en-3-yl or 1-methyl-piperidin-4-yl, R10 hydrogen, 1–4C-alkyl, —OR13, furanyl, indolyl, pyridyl or pyridyl substituted by R18 and/or R19, R11 is —N(R14)R15, R12 is —N(R14)R15, tetrahydrofuranyl or pyridinyl, R13 is 1–4C-alkyl, R14 is hydrogen, 1–4C-alkyl, 3–7C-cycloalkyl or 3–7C-cycloalkylmethyl, R15 is hydrogen, 1–4C-alkyl, 3–7C-cycloalkyl or 3–7C-cycloalkylmethyl, or R14 and R15 together and with inclusion of the nitrogen atom to which they are bonded, form a 4-morpholinyl-, 1-pyrrolidinyl-, 1-piperidinyl- or 1-hexahydroazepinyl-ring, Aryl is phenyl, pyridyl, pyrimidinyl, phenyl substituted by R16 and/or R17, pyridyl substituted by R18 and/or R19, R16 is halogen, nitro, 1–4C-alkyl, trifluoromethyl or 1–4C-alkoxy, R17 is halogen or 1–4C-alkyl, R18 is halogen, nitro, 1–4C-alkyl, trifluoromethyl or 1–4C-alkoxy, R19 is halogen or 1–4C-alkyl, Hetaryl is indol-4-yl, 2-methyl-quinolin-4-yl, 5-chloro-6-oxo-1-phenyl-1,6-dihydro-pyridazin-4-yl, 3-phenyl-1,2,4-thiadiazol-5-yl or 3-o-tolyl-1,2,4-thiadiazol-5-yl, n is an integer from 1 to 4, m is an integer from 1 to 4, s is 1, X is —C(O)— or —S(O)$_2$—, or a hydrate, salt, or hydrate of a salt thereof.

3. A compound of formula I according to claim 1 in which

R1 and R2 together form an additional bond,

R3 represents a benzene derivative of formula (a) or (b)

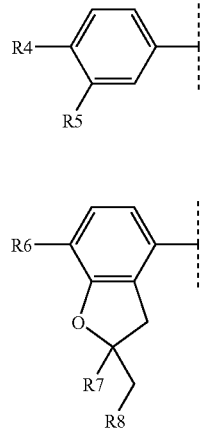

wherein
R4 is methoxy or ethoxy,
R5 is methoxy or ethoxy,
R6 is methoxy,
R7 is methyl and
R8 is hydrogen,
or wherein
R7 and R8 together and with inclusion of the two carbon atoms, to which they are bonded, form a cyclopentane or cyclohexane ring,
A is a bond or methylene (—CH$_2$—),
R9 is phenyl, pyrid-2-yl, pyrid-4-yl, pyrimidin-2-yl, 3-dimethylaminopropyl, 2-dimethylaminoethyl, dimethylaminocarbonylmethyl, furan-2-yl-methanoyl, formyl, ethoxycarbonyl, 5-nitropyridin-2-yl, 3,5-dichloropyridin-4-yl, 2-(morpholin-4-yl)ethyl, 3-(morpholin-4-yl)propyl, 2-morpholin-4-yl-2-oxo-ethyl, 2-oxo-2-pyrrolidin-1-yl-ethyl, 1H-indol-4-yl, tetrahydrofuran-2-ylmethyl, 2-(pyrrolidin-1-yl)-ethyl, pyridin-4-ylmethyl, 2-methyl-quinolin-4-yl, 1-methyl-piperidin-4-yl, 5-trifluoromethyl-pyridin-2-yl, 5-chloro-6-oxo-1-phenyl-1,6-dihydro-pyridazin-4-yl, 3-phenyl-1,2,4-thiadiazol-5-yl, 3-o-tolyl-1,2,4-thiadiazol-5-yl or (E)-3-phenylallyl,
s is 1,
X is —C(O)— or —S(O)$_2$—,
or a hydrate, salt, or hydrate of a salt thereof.

4. A compound of formula I according to claim 1 in which
R1 and R2 together form an additional bond,
R3 represents a benzene derivative of formula (a) or (b)

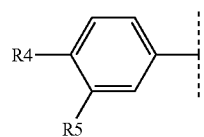

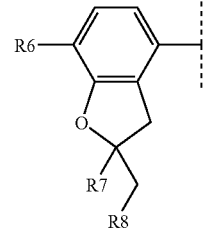

wherein
R4 is methoxy or ethoxy,
R5 is methoxy or ethoxy,
R6 is methoxy,
R7 is methyl and
R8 is hydrogen,
A is a bond,
R9 is phenyl, pyrid-2-yl, pyrid-4-yl, 3-dimethylaminopropyl, 2-dimethylaminoethyl, dimethylaminocarbonylmethyl, furan-2-yl-methanoyl, formyl, ethoxycarbonyl, 5-nitropyridin-2-yl, 3,5-dichloropyridin-4-yl, 2-(morpholin-4-yl)ethyl, 3-(morpholin-4-yl)propyl, 2-morpholin-4-yl-2-oxo-ethyl, 2-oxo-2-pyrrolidin-1-yl-ethyl, 1H-indol-4-yl, tetrahydrofuran-2-ylmethyl, 2-(pyrrolidin-1-yl)ethyl, pyridin-4-ylmethyl, 2-methyl-quinolin-4-yl, 1-methyl-piperidin-4-yl, 5-trifluoromethyl-pyridin-2-yl, 5-chloro-6-oxo-1-phenyl-1,6-dihydro-pyridazin-4-yl, 3-phenyl-1,2,4-thiadiazol-5-yl, 3-o-tolyl-1,2,4-thiadiazol-5-yl or (E)-3-phenylallyl,
s is 1,
X is —C(O)—,
or a hydrate, salt, or hydrate of a salt thereof.

5. A compound of formula I according to claim 1 in which
R1 and R2 together form an additional bond,
R3 represents a benzene derivative of formula (b)

wherein
R6 is methoxy,
R7 is methyl and
R8 is hydrogen,
A is methylene (—CH$_2$—),
R9 is pyrimidin-2-yl, 3-dimethylaminopropyl or 2-(morpholin-4-yl)ethyl,
s is 1,
X is —C(O)—,
or a hydrate, salt, or hydrate of a salt thereof.

6. A compound of formula I according to claim 1 in which
R1 and R2 are both hydrogen or together form an additional bond, R3 represents a benzene derivative of formula (a) or (b)

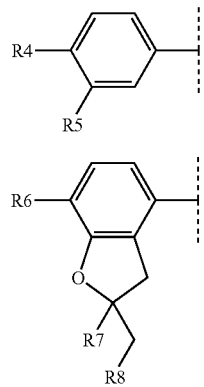

wherein
R4 is 1–4C-alkoxy or 1–4C-alkoxy which is completely or predominantly substituted by fluorine,
R5 is 1–8C-alkoxy, 3–7C-cycloalkoxy, 3–7C-cycloalkylmethoxy, or 1–4C-alkoxy which is completely or predominantly substituted by fluorine,
R6 is 1–4C-alkoxy, 3–5C-cycloalkoxy, 3–5C-cycloalkylmethoxy, or 1–4C-alkoxy which is completely or predominantly substituted by fluorine,
R7 is 1–4C-alkyl and
R8 is hydrogen or 1–4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
A is a bond,
R9 is —C(O)R10, —(CH$_2$)$_m$—C(O)R11, —(CH$_2$)$_n$R12, Aryl, Hetaryl, phenylprop-1-en-3-yl or 1-methyl-piperidin-4-yl,
R10 hydrogen, 1–4C-alkyl, —OR13, furanyl, indolyl, phenyl, pyridyl, phenyl substituted by R16 and/or R17 or pyridyl substituted by R18 and/or R19,
R11 is —N(R14)R15,
R12 is —N(R14)R15, tetrahydrofuranyl or pyridinyl,
R13 is 1–4C-alkyl,
R14 is hydrogen, 1–4C-alkyl, 3–7C-cycloalkyl or 3–7C-cycloalkylmethyl,
R15 is hydrogen or 1–4C-alkyl, 3–7C-cycloalkyl or 3–7C-cycloalkylmethyl,
or R14 and R15 together and with inclusion of the nitrogen atom to which they are bonded, form a 4-morpholiny-, 1-pyrrolidiny-, 1-piperidinyl- or 1-hexahydroazepinyl-ring,
Aryl is phenyl, pyridyl, phenyl substituted by R16 and/or R17, pyridyl substituted by R18 and/or R19,
R16 is halogen, nitro, 1–4C-alkyl, trifluoromethyl or 1–4C-alkoxy,
R17 is halogen or 1–4C-alkyl,
R18 is halogen, nitro, 1–4C-alkyl, trifluoromethyl or 1–4C-alkoxy,
R19 is halogen or 1–4C-alkyl,
Hetaryl is indol-4-yl, 2-methyl-quinolin-4-yl, 5-chloro-6-oxo-1-phenyl-1,6-dihydro-pyridazin-4-yl or 3-phenyl-1,2,4-thiadiazol-5-yl,
n is an integer from 1 to 4,
m is an integer from 1 to 4,
s is an integer from 1 to 2,
X is —C(O)— or —S(O)$_2$—,
or a hydrate, salt, or hydrate of a salt thereof.
7. A compound of formula I according to claim 1 in which
R1 and R2 are both hydrogen or together form an additional bond,
R3 represents a benzene derivative of formula (a) or (b)

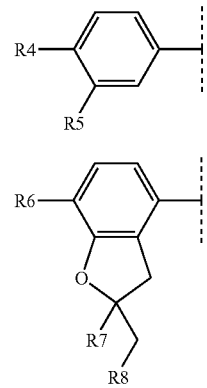

wherein
R4 is 1–2C-alkoxy or 1–2C-alkoxy which is completely or predominantly substituted by fluorine,
R5 is 1–4C-alkoxy,
R6 is 1–2C-alkoxy or 1–2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofurane or tetrahydropyran ring,
A is a bond,
R9 is —C(O)R10, —(CH$_2$)$_m$—C(O)R11, —(CH$_2$)$_n$R12, Aryl, Hetaryl, phenylprop-1-en-3-yl or 1-methyl-piperidin-4-yl,
R10 hydrogen, 1–4C-alkyl, —OR13, furanyl, indolyl, pyridyl or pyridyl substituted by R18 and/or R19,
R11 is —N(R14)R15,
R12 is —N(R14)R15, tetrahydrofuranyl or pyridinyl,
R13 is 1–4C-alkyl,
R14 is hydrogen, 1–4C-alkyl, 3–7C-cycloalkyl or 3–7C-cycloalkylmethyl,
R15 is hydrogen or 1–4C-alkyl, 3–7C-cycloalkyl or 3–7C-cycloalkylmethyl,
or R14 and R15 together and with inclusion of the nitrogen atom to which they are bonded, form a 4-morpholinyl-, 1-pyrrolidinyl-, 1-piperidinyl- or 1-hexahydroazepinyl-ring,
Aryl is phenyl, pyridyl, phenyl substituted by R16 and/or R17, pyridyl substituted by R18 and/or R19,
R16 is halogen, nitro, 1–4C-alkyl, trifluoromethyl or 1–4C-alkoxy,
R17 is halogen or 1–4C-alkyl,
R18 is halogen, nitro, 1–4C-alkyl, trifluoromethyl or 1–4C-alkoxy,
R19 is halogen or 1–4C-alkyl,
Hetaryl is indol-4-yl, 2-methyl-quinolin-4-yl, 5-chloro-6-oxo-1-phenyl-1,6-dihydro-pyridazin-4-yl or 3-phenyl-1,2,4-thiadiazol-5-yl, n is an integer from 1 to 4,
m is an integer from 1 to 4,
s is 1,
X is —C(O)— or —S(O)$_2$—,
or a hydrate, salt, or hydrate of a salt thereof.

8. A compound of formula I according to claim 1 in which
R1 and R2 together form an additional bond,
R3 represents a benzene derivative of formula (a) or (b)

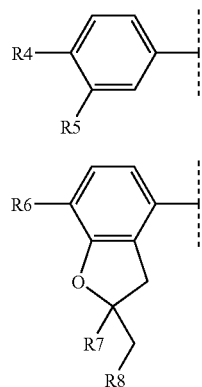

wherein
R4 is methoxy or ethoxy,
R5 is methoxy or ethoxy,
R6 is methoxy,
R7 is methyl and
R8 is hydrogen,
or wherein
R7 and R8 together and with inclusion of the two carbon atoms, to which they are bonded, form a cyclopentane or cyclohexane ring,
A is a bond,
R9 is phenyl, pyrid-2-yl, dimethylaminopropyl, dimethylaminoethyl, furan-2-yl-methanoyl, formyl, ethoxycarbonyl, 5-nitropyridin-2-yl, 3,5-dichloropyridin-4-yl, 2-(morpholin-4-yl)ethyl, 3-(morpholin-4-yl)propyl, indol-4-yl, tetrahydrofuran-2-ylmethyl, 2-(pyrrolidin-1-yl)ethyl, pyridin-4-ylmethyl, 2-methyl-quinolin-4-yl, 1-methyl-piperidin-yl, 5-trifluoromethyl-pyridin-2-yl, 5-chloro-6-oxo-1-phenyl-1,6-dihydro-pyridazin-4-yl, 3-phenyl-1,2,4-thiadiazol-5-yl or phenylprop-1-en-3-yl,
s is 1,
X is —C(O)— or —S(O)$_2$—,
or a hydrate, salt, or hydrate of a salt thereof.

9. A compound of formula I according to claim 1 in which
R1 and R2 together form an additional bond,
R3 represents a benzene derivative of formula (a) or (b)

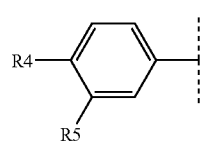

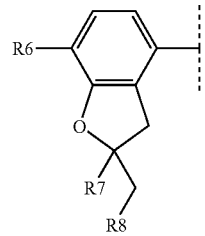

wherein
R4 is methoxy or ethoxy,
R5 is methoxy or ethoxy,
R6 is methoxy,
R7 is methyl and
R8 is hydrogen,
A is a bond,
R9 is phenyl, pyrid-2-yl, dimethylaminoethyl, dimethylaminopropyl, furan-2-yl-methanoyl, formyl, ethoxycarbonyl, 5-nitropyridin-2-yl, 3,5-dichloropyridin-4-yl, 2-(morpholin-4-yl)ethyl, 5-chloro-6-oxo-1-phenyl-1,6-dihydro-pyridazin-4-yl, 3-phenyl-1,2,4-thiadiazol-5-yl or phenylprop-1-en-3-yl,
s is 1,
X is —C(O)— or —S(O)$_2$—,
or a hydrate, salt, or hydrate of a salt thereof.

10. A compound of formula I according to claim 1 in which the hydrogen atoms in the positions 4a and 8a are cis-configurated, or a hydrate, salt, or hydrate of a salt thereof.

11. A compound of formula I according to claim 1 in which the absolute configuration (according to the rules of Cahn, Ingold and Prelog) is S in the position 4a and R in the position 8a, or a hydrate, salt, or hydrate of a salt thereof.

12. A method of treating asthma, COPD, rheumatoid arthritis, dermatoses or Crohn's disease in a patient comprising administering to a patient in need thereof a therapeutically effective amount of a compound of formula I as claimed in claim 1 or a pharmaceutically acceptable hydrate, salt, or hydrate of a salt thereof.

13. A pharmaceutical composition comprising one or more compounds of formula I according to claim 1, or a pharmaceutically acceptable hydrate, salt, or hydrate of a salt thereof together with one or more pharmaceutically acceptable auxiliaries and/or carrier materials.

14. A method of treating asthma and/or COPD in a patient comprising administering to a patient in need thereof a therapeutically effective amount of a compound of formula I as claimed in claim 1 or a pharmaceutically acceptable hydrate, salt, or hydrate of a salt thereof.

* * * * *

UNITED STATES PATENT AND TRADEMARK OFFICE
CERTIFICATE OF CORRECTION

| | |
|---|---|
| PATENT NO. | : 7,022,696 B2 |
| APPLICATION NO. | : 10/475656 |
| DATED | : April 4, 2006 |
| INVENTOR(S) | : Grundler et al. |

It is certified that error appears in the above-identified patent and that said Letters Patent is hereby corrected as shown below:

Claim 6, Column 29, Lines 52-53, Please delete "4-mor-pholiny-, 1-pyrrolidiny-," and replace with -- 4-morpholinyl-, 1-pyrrolidinyl-, --

Signed and Sealed this

Eleventh Day of July, 2006

JON W. DUDAS
*Director of the United States Patent and Trademark Office*